United States Patent [19]

Morse et al.

[11] 4,142,939

[45] Mar. 6, 1979

[54] METHOD OF PRODUCING AN R-TYPE BACTERIOCIN AND ITS USE IN THE DETECTION OF SPECIFIC MICROORGANISMS

[75] Inventors: Stephen A. Morse; Barbara Iglewski, both of Portland, Oreg.

[73] Assignee: Oregon State Board of Higher Education, An agency of the State of Oregon, Eugene, Oreg.

[21] Appl. No.: 672,292

[22] Filed: Mar. 31, 1976

[51] Int. Cl.$^2$ .................... C12D 13/06; G01N 31/00; C12K 1/04

[52] U.S. Cl. ............................. 195/96; 195/103.5 A; 195/103.5 M; 195/104; 195/122

[58] Field of Search ................ 195/103.5 R, 103.5 M, 195/103.5 A, 103.5 K, 96, 81, 80 R, 104, 122

[56] References Cited

PUBLICATIONS

Kanchukh, et al., "Determination of Pesticin and Antibodies to it in the Microprecipitation Reaction", *Chemical Abstracts*, vol. 83, No. 9, p. 361 (1975) Abs. No. 75150w.

Jetten, et al. "Characteristics of the Killing Effect of a *Staphylococcus epidermidis* Bacteriocin", *Chemical Abstracts*, vol. 81, No. 5, p. 100 (1974) Abs. No. 21627x.

Jetten, et al., "Characterization and Extrachromosomal Control of Bacteriocin Production in *Staphylococcus aureus*", *Chemical Abstracts, vol. 79, No. 23, p. 139 (1973) Abs. No. 134162u.*

Walstad, et al., "Growth Inhibition among Strains of *Neisseria gonorrhoeae* Due to Production of Inhibitory Free Fatty Acids and Lysophosphatidylethanolamine, Absence of Basteriocins," *Chemical Abstracts*, vol. 81, No. 25, p. 256 (1974), Abs. No. 165950v.

Ito, et al., "Isolation and Characterization of Pyocins from Several Strains of *Pseudomenas aeruginosa*", *J. Gen. Appl. Microbiol.,* vol. 16, (1970), pp. 205–214.

Jetten, et al., "Production and Purification of a *Staphylococcus epidermidis* Bacteriocin," *J. of Bact.,* vol. 112, No. 1, (1972) pp. 235–242.

Jetten et al., "Nature and Properties of a *Staphylococcus epidermidis* Bacteriocin", J. of Bact., vol. 112, No. 1, (1977), pp. 243–250.

Reeves, "The Bacteriocins", Bacteriol. Rev., vol. 29, No. 1, Am. Soc. Microbiology, (1965), pp. 24–45.

*Primary Examiner*—Thomas G. Wiseman
*Attorney, Agent, or Firm*—Bruno J. Verbeck

[57] ABSTRACT

A method of detecting a specific microorganism comprising contacting said microorganism with bacteriocins from a microorganism of a genus which is taxonomically unrelated to said specific organism. The result of such contact may be utilized to detect the presence of a microorganism belonging to a taxonomically unrelated genus. Radio-labeled or fluorescein-labeled bacteriocins can be reacted with specific bacteria in a biological sample and the presence of such specific bacteria detected by removing excess bacteriocins and determining the presence of fluorescent or radioactive bacteria in the sample. *Neisseria gonorrhoeae* is identified by spotting bacteriocins on a plate of clinical material; or using a disk impregnated with bacteriocins placed on a plate inoculated with the clinical material; or the bacteriocins can be incorporated into one-half of a split agar plate, the identification being made on the basis of a zone of inhibition surrounding the spot where the bacteriocins were applied, or growth inhibition on the portion of the plate to which the bacteriocins were added.

18 Claims, 5 Drawing Figures

METHOD OF PRODUCING AN R-TYPE BACTERIOCIN AND ITS USE IN THE DETECTION OF SPECIFIC MICROORGANISMS

BACKGROUND OF THE INVENTION

1. Field of the Invention

This invention relates to the field of diagnostic microbiology and particularly to diagnostic methods for detecting the presence of, and typing of, a microorganism belonging to a specific genus in a biological sample, and to methods for identifying antigens which are common to taxonomically unrelated genera.

2. Brief Description of the Prior Art

The presence of bacteriocin-like activity in isolates of *Neisseria gonorrhoeae* has been reported by Flynn and McEnteggart, J. Clin. Path. 25:60-61; (1971). Substances from other organisms have also been reported to exhibit bacteriocin-like activity against *N. gonorrhoeae*. Volk and Kraus, Brit. J. Vener. Dis. 49:511-512 (1973) reported the in vitro inhibition of *N. gonorrhoeae* by a substance from *N. meningitidis*. Geizer, J. Hyg. Epid. 12:241-243 (1968) has reported the inhibition of gonoccocal growth by unidentified substances produced by strains of a number of organisms including *Pseudomonas aeruginosa*. The bacteriocin-like activity exhibited against many strains of *N. gonorrhoeae* was attributed to the production of inhibitory levels of free fatty acids and lysophosphatidyethanolamine as reported by Walstad, et al., Infect. Immunity, 10:481-488 (1974).

(a) Origin and Structure of Bacteriocins

Bacteriocins are a group of specific bacteriacidal substances produced by many bacterial during growth. They are proteins of varying molecular weight. Bacteriocins have antibiotic properties, but in contrast to antibiotics which are in clinical use, are much more specific, acting only on members of the same or closely related species. They are extracellular substances which become bound to receptor sites of susceptible organisms. Bacteriocins usually remain contained within the producer strain until released by cell lysis. These extracellular substances can then bind to receptor sites of susceptible organisms. Some bacteriocins closely resemble parts of bacteriophage when examined microscopically. Their production can be induced by agents which interfere with metabolism, such as ultra violet light, mytomicin C, nitrogen mustard and many other agents.

There are two basic types of bacteriocins. One type is a small molecule which is thermo-stable, which cannot be sedimented in the ultra centrifuge, and is not easily resolved by the electron microscope. The other, R-type, is larger and resembles phage tails. This difference in basic types is well illustrated by comparing Colicin V with Colicin 15 (colicins being bacteriocins specific to coliform organisms). Colicin V forms a dialyzable product which has a low molecular weight. Colicin 15 is sedimentable, has a molecular weight of 200,000 and, on electron microscopy, resembles the tail structure of a phage.

Small quantities of bacteriocins are released in normal cultures of organisms, and are presumably released during normal lysis found during degeneration of organisms in culture. Their genetic determinants exist as an extra chromosomal element which replicate in phase with bacterial chromosomes, and therefore persist as long as the strain persists. They are released in quantity by lysis of the bacterial cell whether this occurs by phage infection, the action of bacteriolytic agents, such as metabolic inhibitors, or other factors.

Chemically, all bacteriocins are macromolecular and contain polypeptide, protein, other radicals such as carbohydrate, phosphate and lipopolysaccharide which contributes to the ultimate size of the molecule.

(b) Nomenclature

While classification and nomenclature are necessarily undergoing change as more evidence of their origin, chemistry and activities accumulate, bacteriocins are named, as a general rule, on the specific rather than generic name of the originating organisms. For example, *E. coli* bacteriocins are termed colicins. *Serratia marcescens* give marcesins; Enterobacteraerogenes, aerocins; *Pseudomonas aeruginosa* (pyocyaneus), pyocins; *Listeria monocytogenes*, monocins; Staphylococcus sp., staphylocins, etc.

This classification began after Gratia in Belgium first reported that filtrates of a particular strain of *E. coli* inhibited growth of the same species, the inhibiting factor being called a colicin. Some 20 colicins were subsequently recognized and classified as A-V. Each colicin was specific for a small group of strains of Enterobacteraciae. Each bacteriocin whether from *E. coli* or other species appears to be specific in action to the same, or to taxonomically related, species of organisms.

(c) Assay of Bacteriocins

The concentration of bacteriocin in a filtrate titrated by placing a drop (10-20 $\mu$l) on a lawn culture inoculated witn indicator bacteria ($10^7$/ml) of freshly grown cells. After incubation for 18-24 hours at 37° C the plates are read and scored. Titers are regarded as a reciprocal of the highest dilution that yields a clear spot. Another method is to add bacteriocin to an enumerated excess of sensitive organisms, the bacteriacidal activity being proportional to the quantity of bacteriocin present.

One unit of bacteriocin activity is the lowest concentration which completely inhibits growth of an indicator strain.

At the present time purification is more a matter of concentration from the original broth or saline suspensions then isolation of specific fractions. The most commonly used method to remove the cells by centrifugation after 6-24 hours of incubation. Purification is completed by column chromatography following ammonium sulfate precipitation followed by dialysis against equilibration buffer.

Purified bacteriocins are stable in a lyophilized state for long periods of time. In solution they are stable at 4° C and pH 7.0 for 6 weeks. Bacteriocin are not irreversibly denatured by 4M guanidine thiocyanate or 6M urea, but are completely inactivated at 60° C and pH 7.0 in 60 minutes.

(e) Mode of Action

Bacteriocins act on cells which are in the logarithmic phase of proliferation. The treatment of sensitive cells rapidly inhibits incorporation of labeled leucine and thymidine into acid insoluble materials. The time required for inhibition of $^{14}$C and $^3$H labeled isotopes is dependent upon the concentration of bacteriocins. It has been established that both DNA and protein synthesis are blocked by bacteriocin. When organisms in cultures are exposed to bacteriocin, they do not incorporate $^{14}$C leucine into the protein or $^3$H thymidine into DNA. This is probably due to interference with the active transport of leucine and thymidine by the specific bacteriocin. Concurrently the concentration of ATP falls to 10–15% of control value. This is not related to a decline in macromolecular synthesis, but does help to explain the faltering energy transport mechanisms which are seen in bacterial cells exposed to bacteriocins. Though ATP activity is inhibited, the phosphotransferase system is not affected and a-methyl D-glucoside has been shown to accumulate in coliforms. Apart from these modes of activity, interference with cell membrane integrity may occur in some species of susceptible organisms.

SUMMARY OF THE INVENTION

An object of the present invention is to provide a new and unique method for inhibiting the growth of microorganisms. Another object is to provide an improved test for detecting the presence in a biological sample of a microorganism belonging to a particular genus. It is a further object to provide an improved test for the identification of *Neisseria gonorrhoeae*. Another object is to provide a means for typing of *Neisseria gonorrhoeae*. A still further object is to provide a test for the identification of common bacterial antigens. A still further object is to provide test means for demonstrating the presence or absence of common antigens or surface components, mammalian cells. A still further object is to provide a new and unique pyocin which inhibits the growth of *N. gonorrhoeae*.

BRIEF DESCRIPTION OF THE DRAWINGS

This invention will be more fully understood by the following description and the attached drawings, in which.

DESCRIPTION OF THE PREFERRED EMBODIMENTS

Figure 1:
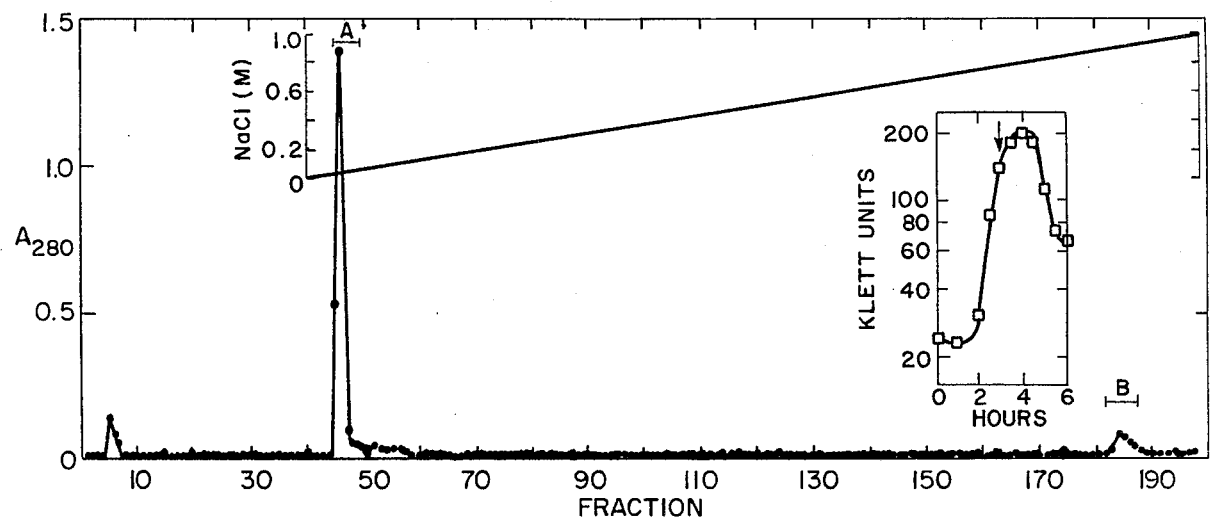
FIG. 1 is a chart illustrating purification of R-type pyrocin (611 131) by DEAE-cellulose chromatography. Fractions containing inhibitory activity are indicated by A and B. The insert shows the induction of pyocin production in *Pseudomonas aeruginosa* ATCC 29260 by mitomycin C (1 μg/ml). The arrow indicates the time of mitomycin C addition.

In accordance with the invention, the foregoing and other objects are accomplished as hereinafter described.

One embodiment of the invention is represented by a method for inhibiting the growth of a microorganism belonging to a specific genus which method comprises contacting that organism with a bacteriocin from a microorganism of a taxonomically unrelated genus, which binds to the first said microorganism, that method being hereinafter described as follows:

Bacteriocin, Organisms and Media

The bacteriocin was an R-type pyocin (611 131) obtained from a strain of *P. aeruginosa* (ATCC 29260).

The basal medium contained the following per liter: proteose peptone no. 3 (Difco), 15 g; $K_2HPO_4$, 4 g; $KH_2PO_4$, 1 g; NaCl, 5 g; and soluble starch, 1 g. The final pH of the medium was 7.2. When used for the production of R-type pyocins by *P. aeruginosa*, glycerol (1% vol/vol) and monosodium glutamate (8.46 g/liter) were added after autoclaving. When used for the growth of *Neisseria* spp., growth factor supplement (1% vol/vol), identical in composition to IsoVitaleX enrichment (BBL) but lacking glucose; $NaHCO_3$ (42 mg/liter), and glucose (5 g/liter), was added after autoclaving. GC agar (Difco) plates containing glucose (5 g/liter) and growth factor supplement (1% vol/vol) were used where indicated.

Induction and Purification of R-type Pyocin (611 131)

An overnight culture of *P. aeruginosa* ATCC 29260 was centrifuged (2,100 × g for 10 min.) and resuspended to one-tenth the original volume in a solution containing 0.85% NaCl and 0.1% cysteine hydrochloride at pH 6.5. A 1% (vol/vol) inoculum was used and the culture incubated on a gyrotory shaker at 37° C. When the turbidity of the culture reached approximately 150 Klett units, mitomycin C was added at a final concentration of 1 μg/ml. Incubation was continued until extensive lysis of the culture occurred, this normally occurring within 3 hours after the addition of mitomycin C. The mitomycin C-induced culture was centrifuged at 2,400 × g for 30 minutes to remove cellular debris and the resulting supernatant treated with chloroform (5% vol/vol). This supernatant fraction was designated crude pyocin.

The crude pyocin preparation was further purified by a modification of a method of Kageyama and Egami, Life, Sci. 9:471–476 (1962). Briefly, this procedure consisted of the slow addition of 1 M $MnCl_2$ (60 ml per liter of lysate), while stirring, to the crude pyocin preparation. After adjusting the pH to 7.5 with 1 M NaOH, the resulting precipitate was removed by centrifugation (2,400 × g for 15 min.). The supernatant was designated partially purified pyocin.

Further purification was accomplished by the addition of $(NH_4)_2SO_4$ to 70% saturation and incubating overnight at 4° C. After centrifugation (2,400 × g for 30 min.) at 4° C, the pellet containing the pyocin activity was dissolved in 50 ml of 0.01 M tris(hydroxymethyl)aminomethane (Tris)hydrochloride (pH 7.5) containing 0.01 M $MgCl_2$ and 0.01 M $MgSO_4$ and dialyzed overnight at 4° C against 2 liters of the same buffer. If necessary, the preparation was clarified by centrifugation (2,400 × g for 15 min. at 4° C). The pyocin preparation was then centrifuged at 100,000 × g for 90 min. (type 40 rotor, Spinco model L2-65B ultracentrifuge). The gelatinous pellet was gently dissolved in 20 ml of buffer and chromatographed on DEAE-cellulose (DE-52, Whatman Biochemicals Ltd., Kent, England) previously washed and equilibrated with the same buffer. A 8 ml sample of pyocin was applied to a 1.5 × 28 cm column and allowed to adsorb for 1 hour. The column was washed with 200 ml of buffer to remove material not adsorbing to the DEAE-cellulose. The pyocin was then eluted with 800 ml of a NaCl gradient (0 to 1.0M) in 0.01 M buffer. Five-ml fractions were collected and analyzed for absorbance at 280 nm and for pyocin activity. The fractions exhibiting pyocin activity were pooled, dialyzed against 0.01 M Tris buffer (pH 7.5) to remove NaCl, and the concentrated by ultracentrifugation (1,000,000 × g for 90 min.). All chromatographic procedures were carried out at 4° C. (FIG. 1).

Pyocin Typing

Pyocin typing was performed using the broth method described by Jones, et al. Appl. Microbiol. 27: 400–406 (1974). The ALA set of 18 strains of P. aeruginosa was used for indicator strains. The pyocin type and pattern are reported by the notation described by Farmer and Herman, J. Infect. Dis. 130:543–546 (1974).

Assay of Pyocin Activity

The strains of N. gonorrhoeae being tested for susceptibility to the pyocin were grown overnight on GC agar plates. A suspension of these organisms was prepared in a diluent consisting of 0.85% NaCl and 0.1% HCl (pH 6.4) and adjusted to a Klett reading of 50–60. GC agar plates were inoculated by means of a swab dipped into the cell suspension. Undiluted or serially diluted pyocin preparations (5 μl) were applied to the surface of the agar plate. All plates were incubated overnight at 37° C with increased $CO_2$ (5% $CO_2$) prior to being read. Pyocin titers are expressed as 200 times the reciprocal of the highest dilution which shows complete inhibition.

Electron Microscopy

Figure 2:
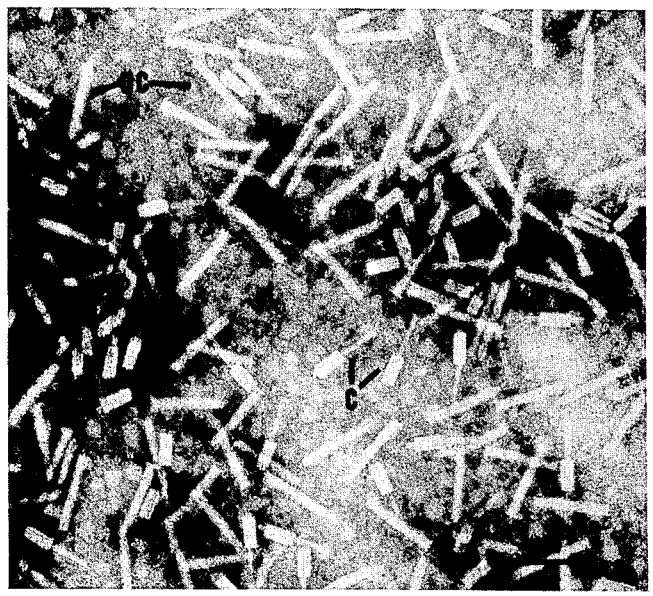
FIG. 2 is an electron micrograph of a negative-stained preparation of R-type pyocin 611 131. Symbols: uc uncontracted pyocin; c. contracted pyocin; Bar = 0.1 μm.

Pyocins were prepared for examination in an electron microscope by the negative staining technique of Brenner, et al., Biochim. Biophys. Acta. 34:103–110 (1959). Pyocin preparations were centifuged at 100,000 × g for 1 hour and the pellet resuspended in a small volume of 1 M $HN_4$ $C_2H_3O_2$ (pH 7.0). Formvar-covered copper grids were placed onto a drop of the sample for 1–2 minutes and then blotted dry with filter paper. These grids were then placed onto a drop of 1.5% sodium phosphotungstate (pH 7.0) for 30 seconds. Excess fluid was removed with filter paper. Samples were examined in a Phillips EM-200 electron microscope at 60 kv. (FIG. 2).

The interaction of pyocins with cells of N. gonorrhoeae was observed by a similar procedure. Thirty minutes after the addition of pyocin to a liquid culture of N. gonorrhoeae 72H870, a sample was removed and treated as above. The negative-stained preparation was examined in an RCA electron microscope at 50 Kv.

Table 1 describes results of the production of the gonoccocal inhibitory factor synthesized during the growth of P. aeruginosa ATCC 29260 in the medium above described. The addition of mitomycin C (1 μg/ml) caused extensive lysis of the culture within three hours and resulted in a 16-fold increase of the concentration of the inhibitory factor determined by titration on P. aeruginosa PS7 and N. gonorrhoeae strains JW-31 and DG1 1947. Also shown in Table 1 the titer of the inhibitory factor varied with different strains of N. gonorrhoeae, no difference being observed with colonial variants of a single strain.

Table 1.
Effect of mitomycin C on the production of gonococcal inhibitory factor by Pseudomonas aeruginosa ATCC 29260.

| Organism | Inhibitory Titer (Units/ml) Non-induced | Induced |
|---|---|---|
| P. aeruginosa PS-7 | 2560 | s40,960 |
| N. gonorrhoeae JW-31 | 2560 | 40,960 |
| N. gonorrhoeae DGI 1947 | 640 | 10,240 |
| N. gonorrhoeae 1138 (T-1) | N.D.[b] | 5,120 |
| N. gonorrhoeae 1138 (T-4) | N.D. | 5,120 |

[a] Mitomycin C (1 μg per ml of medium), when serially diluted, ceased to inhibit the growth of these organisms at 1:2 dilution (0.5 μg/ml).
[b] N.D. = not determined.

The inhibitory factor was partially purified from supernatants of the mitomycin C-induced cultures of P. aeruginosa strain ATCC 29260 by the procedure described above. The inhibitory factor was eluted from the DEAE cellulose with a NaCl gradient of 0 to 1.0 M. (FIG. 1). Two peaks containing the inhibitory factor were observed. The major peak (A) eluted at a NaCl concentration of 0.06 M and contained more than 90% of the inhibitory activity. A minor peak (B) eluted at a NaCl concentration of 0.91 M and contained less than 10% of the activity. The fractions comprising peak A were pooled, dialyzed against 0.01 Trishydrochloride buffer (pH 7.5) to remove the NaCl and concentrated by ultracentrifugation (100,000 × g for 90 min.). This preparation was used in the hereinafter described tests.

Examination in the electron microscope of negatively stained preparation of the purified inhibitory factor showed that the particles resembled R-type pyocins in both the uncontracted and contracted states (FIG. 2). In the uncontracted state these particles measured 111.5 nm in length by 15.3nm in width. In the contracted state the particles consisted of an inner core (105 nm in length × 6.5 nm in width) surrounded by a contracted sheath (44.4 nm in length by 18.6 nm in width). Between 20 and 30 percent of the particles observed in these preparations were in the contracted state. Neither intact bacteriophage nor bacteriophage ghosts were seen in any of the negative-stained preparations.

The type of the pyocin in both partially purified and purified preparations were determined as hereinbefore described, the results indicating that the pattern did not change during purification. The pyocin pattern is 611 131.

The Effect of Pyocin 611 131 on the Growth of a Clinical Isolate of N. gonorrhoeae (strain 72H870).

Figure 3:
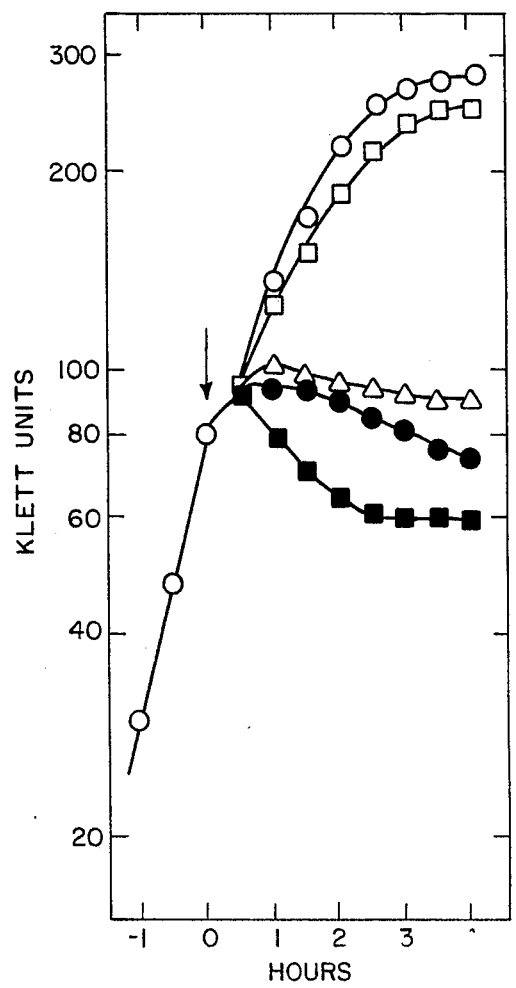
FIG. 3 is a chart showing the effect of R-type pyocin (611 131) on the growth of *N. gonorrhoeae* strain 72H870. Purified pyocin or mitomycin C were added to exponentially growing cultures (1.4 × $10^8$ CFU/ml) of strain 72H870. Symbols: 0, no additions; □ 400 units of pyocin/ml; △ 1,000 units pyocin/ml; ● 4,000 units of pyocin/ml; ■ 20,000 units of pyocin/ml.

The effect of this pyocin on growing cells of this microorganism was determined by the addition of various concentrations of the purified preparation to exponentially growing cultures. FIG. 3 shows a concentration-dependent inhibition of gonococcal growth by the addition of type 611 131 pyocin.

Figure 4:
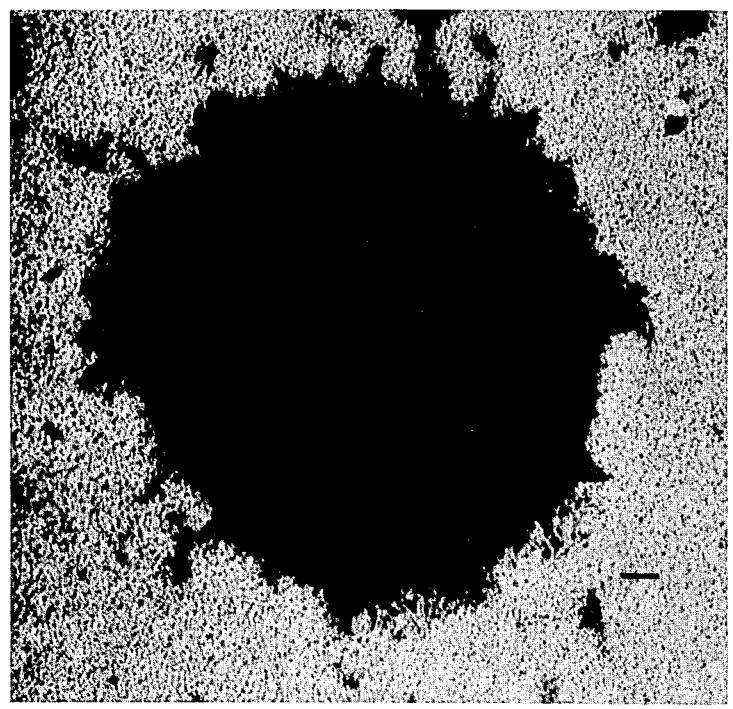
FIG. 4 is a micrograph showing interaction of R-type pyocin 611 131 wiht cells of *N. gonorrhoeae* strain 72H870. Bar = 0.1 μm.

At high pyocin concentration a complete inhibition of growth occurred within one hour accompanied by extensive lysis of the culture. Examination by electron microscopy (FIG. 4) showed that a direct interaction occurred between the pyocin and susceptible cells of N. gonorrhoeae. The pyocin cell interaction results in contraction of the pyocin and suggests that receptors are present on the gonococcal cell surface.

Inhibitory Spectrum of Pyocin Type 611 131.

Figure 5:
FIG. 5 is a photograph showing inhibition of *Neisseria gonorrhoeae* by an R-type pyocin (611 131). Symbols: a. *N. gonorrhoeae* strain JW-31; b. *N. Gonorrhoeae* strain 72H870; c. *N. gonorrhoeae* strain 1138 (colony type T-1); d. *N. gonorrhoeae* strain 1138 (colony type T-4); e. *N. Gonorrhoeae* strain CS-7; f. *P. aeruginosa* strain ATCC 29260.

Aliquots of the purified pyocin preparation were spotted on lawns prepared from clinical isolates of N. gonorrhoeae. Typical patterns of inhibition are shown in FIG. 5. The zone of inhibition was clearly evident in all strains examined. No difference was observed A between colony types T-1 and T-4 from the same strain. A negative control of the producer strain, P. aeruginosa ATCC 29260 was also included.

The inhibition of various Neisseria species by this pyocin is shown in Table 2. All isolates of N. gonorrhoeae, from both disseminated and nondisseminated infections, were inhibited. However, only 3 of 20 strains of N. meningitidis and 5 of 16 strains of N. lactamica were inhibited. No correlation was observed between the serological group and inhibiton of N. meningitidis None of the other five species tested were inhibited by this pyocin.

Table 2.

Sensitivity of various Neisseria species to purified R-type pyocin (611 131) from Pseudomonas aeruginosa strain ATCC 29260.

| Species | Serogroup | Number of Strains Tested | Number of Strains Sensitive |
|---|---|---|---|
| N. gonorrhoeae | — | 56 | 56 |
| N. meningitidis | A | 4 | 0 |
|  | B | 5 | 1 |
|  | C | 3 | 0 |
|  | X | 3 | 0 |
|  | Y | 1 | 1 |
|  | Z | 2 | 1 |
|  | 135 | 2 | 0 |
| N. lactamica | — | 16 | 5 |
| N. mucosa | — | 1 | 0 |
| N. flava | — | 1 | 0 |
| N. subflava | — | 1 | 0 |
| N. ovis | — | 1 | 0 |
| N. flavescens | — | 1 | 0 |

Rapid Identification of Neisseria gonorrhoeae

A method for rapidly identifying Neisseria gonorrhoeae can be carried out by any of the following procedures: pyocin 611 131 is (a) spotted on an agur plate containing the biological sample being tested, or (b) a disk impregnated with the pyocin is placed on a plate inoculated with the sample, or (c) pyocin incorporated into one-half of a split agar plate, is inoculated with the sample. Following incubation, identification of the organism as N. gonorrhoeae is made on the basis of a zone of inhibition surrounding the spot where the pyocin was applied, or inhibition of growth on the portion of the plate into which the pyocin was incorporated.

This method can, of course, be applied to the identification of other bacteria.

Typing of Neisseria gonorrhoeae

The typing of N. gonorrhoeae and other species of Neisseria involves the use of several pyocin types and is based upon the inhibition or non-inhibition of the test organism. The results observed are used to identify the "type" of the isolate by relating them to the results obtained with a series of known types. (Table 3). This method of typing is especially useful in epidemiological studies where the prevalence or appearance of new strains is of importance, as well as in determining whether a treatment failure was due to a resistant organism or to reinfection with a new type.

Table 3.

Typing of Neisseria gonorrhoeae by pyocins from Pseudomonas aeruginosa.

| Organism | Bacteriocin | | | |
|---|---|---|---|---|
|  | 1 | 2 | 3 | 4 |
| Neisseria gonorrhoeae JW31 | — | — | + | — |
| N. gonorrhoeae 72H874 | — | — | + | — |
| N. gonorrhoeae 72H873 | — | — | + | — |
| N. gonorrhoeae 1938 | — | — | + | + |

Table 3.-continued

Typing of Neisseria gonorrhoeae by pyocins from Pseudomonas aeruginosa.

| Organism | Bacteriocin | | | |
|---|---|---|---|---|
|  | 1 | 2 | 3 | 4 |
| N. gonorrhoeae 1567 | — | — | + | — |
| N. gonorrhoeae 2020 | — | — | + | + |
| N. gonorrhoeae 1344 | — | — | + | — |
| N. gonorrhoeae 2024 | +/− | — | + | + |
| N. gonorrhoeae 1817 | — | — | + | + |
| N. gonorrhoeae 1947 | + | — | + | + |
| N. gonorrhoeae 1402 | — | — | + | +/− |
| N. gonorrhoeae 1918 | — | — | + | — |
| N. gonorrhoeae 1451 | — | — | + | — |

Bacteriocin 1: Ps. aeruginosa FS-5
Bacteriocin 2: Ps. aeruginosa FS-6
Bacteriocin 3: Ps. aeruginosa ATCC 29260
Bacteriocin 4: Ps. aeruginosa PS-7

Further embodiments of the invention are described hereinafter:

Identification of N. gonorrhoeae using Fluorescein-labelled Pyocins.

In this method pyocins produced and purified as described above are fluorescein labelled in accordance with the method of Johnson, et al. "Handbook of Experimental Immunology." Blackwell Scientific Publications, Oxford 1973. The thus labelled pyocins are reacted with suspected N. gonorrhoeae on a slide prepared from clinical material or from isolated colonies from an agar plate. Excess pyocins are removed by rinsing the slide with .02 molar phosphate buffered saline (pH 7.2) buffer, and the slide observed under a UV microscope. Cells having the typical morphology of N. gonorrhoeae and showing fluorescense are considered positive for N. gonorrhoeae.

Identification of bacteria by radio-labeled pyocins.

Radioactive pyocins are prepared by iodinating them with $^{125}$I by the chloramine T method. Alternatively, they can be prepared labeled with $^3H$ or $^{14}C$ by incorporating specifically labeled amino acids into the growth medium prior to induction of pyocin synthesis in Pseudonomas aeruginosa by mitomycin C. Pyocins produced by this method are radioactive. Specific bacteria are readily identified by reacting the radioactive pyocins with a suspension of the bacteria. This suspension is then subjected to membrane filtration or centrifugation to separate unbound pyocins from those which have bound specifically to the surface of bacterial cells. The filter or washed cell pellet is then counted to determine the amount of labeled pyocin bound. The data is compared with the degree of nonspecific binding; any increase over the level of non-specific binding indicates the presence of the unknown organism.

The invention can be utilized in the identification of antigens which are common to bacteria of taxonomically unrelated genera. Bacteriocins are known to bind to specific receptor sites on the outer surface of bacteria. These receptor sites are also exposed to the host's defense mechanisms and may thus stimulate the production of antibodies which may be either bactericidal or opsonizing types. Bacteria may share common antigens. These common antigens may also be the bacteriocin receptor sites, therefore the interaction of bacteriocins with diverse species of bacteria may be used as an indicator of shared antigens. (Table 4). This may in turn be used in the isolation and purification of antigens for vaccine production. Thus a minor antigen or one organism may be a major antigen on another and therefore easier to purify and obtain in large quantities.

Table 4.

Interaction of bacteriocins with diverse species of bacteria.

| Organism | Bacteriocin | | |
|---|---|---|---|
| | 1 | 2 | 3 |
| *Aeromonas hydrophilia* | + | + | + |
| *Enterbacter aerogenes* | − | + | + |
| *E. cloaceae*CP | + | − | + |
| *E. coli*B | + | + | + |
| *El coli*Sears | − | − | + |
| *Providencia stuartii* | + | − | + |
| *Ps. Aeruginosa non pigm* | + | + | + |
| *Ps. maltophilia*B | +/− | + | + |
| *Sal. chloerasuis* | − | + | + |
| *Brucella abortus* | − | − | + |
| *B. bronchisepticus* | − | − | − |
| *B. suis* | + | + | + |

Bacteriocin 1: Vibrio cholera El Tor
Bacteriocin 2: Serratia marcescens
Bacteriocin 3: Aeromonas hydrophilia The methods of the invention may also be used to demonstrate common antigens (or surface components) in mammalian cells. Because of the inherent specificity of their receptors, bacteriocins may be used in place of compounds such as lectins or in procedures involving tissue typing.

The invention may also be used in the identification of other bacteria. Thus as shown in Table 4, bacteriocins from *Vibrio cholerae, Aeromas hydrophila,* and *Serratia marcescens* will cross react with toxonomically unrelated organism.

In view of all of the above, it is evident that the several objects of the invention are achieved and various other advantageous results attained.

Since various changes can be made in the above-described methods without departing from the scope of the invention, it is intended that all matter contained in the above description be interpreted as illustrative and not in a limiting sense.

What is claimed is:

1. The method of obtaining bacteriocin having bacteriacidal activity against *Neisseria gonorrhoeae* which comprises broth-culturing *Pseudomonas aeruginosa* ATCC 29260, removing supernatant from said culture, purifying said supernatant, and separating a bacteriocin-rich fraction therefrom.

2. The method of claim 1 wherein said culturing uccurs in the presence of mitomycin A whereby the concentration of a bacteriocin is increased.

3. The method of claim 1 wherein said purification comprises salt fractionation, chromatography on DEAE-cellulose and sedimentation by centrifugation.

4. A method of inhibiting the growth of a bacteria belonging to a specific genus which comprises the step of contacting said bacteria with an R-type bacteriocin recovered from a taxonomically unrelated genus of bacterium which binds to the first said bacteria.

5. A method of inhibiting the growth of *Neisseria gonorrhoeae* which comprises the step of contacting *Neisseria gonorrhoeae* with an R-type pyocin which binds thereto.

6. The method of claim 5 wherein said pyocin is from *Pseudomonas aeruginosa* ATCC 29260, and is typable as 611 131.

7. A method of detecting the presence in a biological sample, of a bacteria belonging to a specific genus, which comprises the steps of combining said sample, a microbiological medium capable of supporting growth of said bacteria, and an R-type bacteriocin from a bacteria from a taxonomically unrelated genus of bacterium, which bacteriocin binds to the first said bacteria, incubating the resulting combination, and observing the growth or inhibition of growth of the first said bacteria in contact with said medium.

8. The method of claim 7 wherein the said bacteria to be detected is *Neisseria gonorrhoeae*.

9. The method of claim 8 wherein said bacteriocin is a pyocin.

10. The method of claim 9 wherein said pyocin is from *Pseudomonas aeruginosa* ATCC 29260, typable as 611 131.

11. A method of detecting the presence in a biological sample of a bacteria belonging to a specific genus, which comprises the steps of combining said sample with a labeled R-type bacteriocin from a bacteria of a taxonomically unrelated genus of bacterium which bacteriocin binds to the first said bacteria, separating from the sample the labeled R-type bacteriocins which do not become bound to said bacteria to be detected in the sample, and measuring the amount of labeled bacteriocins either bound to said bacteria to be detected in the sample or separated from said sample in the previous step.

12. The method of claim 11 wherein said bacteriocin is labeled with a radioactive or fluorescent moiety.

13. The method of claim 11 wherein said bacteria to be detected is *Neisseria gonorrhoeae*.

14. The method of claim 13 wherein said bacteriocin is a pyocin.

15. The method of claim 14 wherein said pyocin is from *Pseudomonas aeruginosa* ATCC 29260 and is typable as 611 131.

16. The method of claim 14 wherein said pyocin is labeled with a radioactive or fluorescent moiety.

17. The method of identifying antigens which are common to bacteria of taxonomically unrelated genera, which comprises contacting an R-type bacteriocin with bacteria of a taxonomically unrelated genus, and detecting the interaction of said bacteriocin with the said taxonomically unrelated bacteria by measuring the degree of binding.

18. The method of claim 17 wherein the said antigens are from mammalian cells.

* * * * *